(12) United States Patent
Joo et al.

(10) Patent No.: US 11,622,983 B2
(45) Date of Patent: Apr. 11, 2023

(54) PHARMACEUTICAL COMPOSITION FOR PREVENTING OR TREATING NEURODEGENERATIVE DISEASES INCLUDING FERMENTED STEAM-DRIED GINSENG BERRY

(71) Applicant: Huscion Co., Ltd., Seongnam-si (KR)

(72) Inventors: Seong Soo Joo, Yongin-si (KR); Su Kil Jang, Gangneung-si (KR)

(73) Assignee: Huscion Co., Ltd., Seongnam-Si (KR)

( * ) Notice: Subject to any disclaimer, the term of this patent is extended or adjusted under 35 U.S.C. 154(b) by 0 days.

(21) Appl. No.: 17/105,032

(22) Filed: Nov. 25, 2020

(65) Prior Publication Data

US 2021/0252092 A1  Aug. 19, 2021

(30) Foreign Application Priority Data

Feb. 14, 2020  (KR) .................. 10-2020-0018483

(51) Int. Cl.
*A61K 36/258*  (2006.01)
*A61P 25/28*  (2006.01)

(52) U.S. Cl.
CPC ............ *A61K 36/258* (2013.01); *A61P 25/28* (2018.01); *A61K 2236/33* (2013.01); *A61K 2236/51* (2013.01)

(58) Field of Classification Search
None
See application file for complete search history.

(56) References Cited

U.S. PATENT DOCUMENTS

2016/0022751 A1* 1/2016 Joo .................. A61K 36/258
                                                                514/34

FOREIGN PATENT DOCUMENTS

| CN | 104095894 | 10/2014 |
| CN | 107929339 | 4/2018 |
| EP | 2 982 376 | 2/2016 |
| KR | 2012021944 A | * 3/2012 |
| KR | 10-2016-0081288 A | 7/2016 |
| KR | 10-1785482 | 10/2017 |
| KR | 10-2018-0013716 | * 2/2018 |
| KR | 10-2019-0126713 A | 11/2019 |
| WO | 03/086440 | 10/2003 |

OTHER PUBLICATIONS

Ji Min Jeon et al., "Antioxidant and Antiaging Effect of Ginseng Berry Extract Fermented by Lactic Acid Bacteria", J. Soc. Cosmet, Scientists Korea, Mar. 2011, pp. 75-81, vol. 37, No. 1.
Kim et al., "Steam-Dried Ginseng Berry Fermented with Lactobacillus plantarum Controls the Increase of Blood Glucose and Body Weight in Type 2 Obese Diabetic db/db Mice", J. Agric. Food Chem., vol. 60, 2012, pp. 5438-5445.
Wikipedia, Liquor, at https://en.wikipedia.org/wiki/Liquor (retrieved on May 8, 2022).
Encyclopaedia Britannica, Distilled Spirit, https://www.britannica.com/topic/distilled-spirit (retrieved on May 8, 2022).

* cited by examiner

*Primary Examiner* — Susan Hoffman
(74) *Attorney, Agent, or Firm* — Sughrue Mion, PLLC

(57) ABSTRACT

The present disclosure relates to a pharmaceutical composition for preventing or treating neurodegenerative diseases, the pharmaceutical composition including a fermented steam-dried ginseng berry as an active ingredient. Specifically, the fermented steam-dried ginseng berry may have a high total ginsenoside and polyphenol content, exhibit antioxidant activity, inhibit acetylcholinesterase, improve cognitive function and spatial perception in animal model of dementias, recover acetylcholine expression and inhibit accumulation of amyloid-beta in brain tissue of the animal model of dementias, inhibit brain damage in animal model of dementias, and promote expression of genes related to brain damage in neuronal cell lines, and accordingly, the fermented steam-dried ginseng berry may be used to treat neurodegenerative diseases, improve cognitive function, and protect brain cells.

10 Claims, 16 Drawing Sheets

(1 of 16 Drawing Sheet(s) Filed in Color)

Specification includes a Sequence Listing.

○: Non-treated group
●: Amyloid-beta treated group
▽: Fermented steam-dried ginseng berry 100
□: Fermented steam-dried ginseng berry 300
◇: Fermented steam-dried ginseng berry 500
△: EGCG 100

PHARMACEUTICAL COMPOSITION FOR PREVENTING OR TREATING NEURODEGENERATIVE DISEASES INCLUDING FERMENTED STEAM-DRIED GINSENG BERRY

PRIORITY CLAIM AND CROSS-REFERENCE

This application claims priority under 35 U.S.C. § 119 to Korean Patent Application No. 10-2020-0013483, filed on Feb. 14, 2020, in the Korean Intellectual Property Office (KIPO), the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Nov. 24, 2020, is named Q259506 Sequence Listing.txt and is 2,379 bytes in size.

TECHNICAL FIELD

Aspects of embodiments of the present disclosure relate to a pharmaceutical composition for preventing or treating neurodegenerative diseases that includes fermented steam-dried ginseng berry as an active ingredient.

DISCUSSION OF RELATED ART

Ginseng (i.e., *Panax ginseng* C.A. meyer), a plant belonging to the genus *Panax* in the family Araliaceae, is a herbal medicine that has been used in Korea, China, and Japan to prevent diseases and prolong lifespan since 2,000 years ago. The efficacy and effects of ginseng that have been known to date include, for example, effects on the central nervous system, anti-carcinogenic effects, anti-cancer effects, immune system regulation, anti-diabetic effects, liver function enhancement effects, improvement on cardiovascular disorders, anti-arteriosclerosis effects, blood-pressure regulation effects, improvement on menopause, improvement on osteoporosis, anti-stress effects, anti-fatigue effects, antioxidant activity, anti-aging effects, and the like.

Ginseng berry (e.g., fruit) which is immature until the third year matures after the fourth year, and the medicinal name is ginsengja. Ginseng berry is known to boost vitality, strengthen the body, and delay aging, and it is also known to be effective in improving dizziness, shortness of breath, boils, and lack of energy. However, such ginseng berries are cultivated simply to obtain seeds for ginseng cultivation due to its low utilization in farm. Further, ginseng berries are removed around May or June, except seeds that are harvested for cultivation, in order to prevent the dispersion of active ingredients into flowers and berries, which are reproductive organs, and to induce them to accumulate in the roots. Ginsenoside, a representative bioactive ingredient of ginseng, is evenly distributed in ginseng above and below the ground, but it has been reported that ginsenoside of ginseng berries includes different components and contents from ginseng roots.

More than 30 kinds of ginsenosides have been reported, of which ginsenosides having hydrogen bonded to carbon at position 6 are referred to as protopanaxadiol-type saponins, and ginsenosides having oxygen bonded to carbon at position 6 are referred to as protopanaxatriol-type saponins. General ginsenosides such as Rb1, Rb2, Rc, Rd, Re, etc., which are included in large amounts in ginseng and wild ginseng, are not absorbed directly by the human body, and some are decomposed by intestinal bacteria or enzyme and then converted into ginsenosides F1, F2, Rg3, compound K, etc., to be absorbed.

Accordingly, various studies on pharmacological effects of ginseng berries are being conducted. Specifically, Korean Patent Publication No. 10-2019-0126713 relates to a composition for preventing or inhibiting infection of influenza virus that includes ginseng berry polysaccharide as an active ingredient, and it is disclosed that ginseng berry polysaccharide having a specific component and structure has an effect of inhibiting the activity of neuraminidase.

Meanwhile, neurodegenerative disease refers to a disease that occurs in the brain among degenerative diseases that occur with aging and includes vascular dementia, Alzheimer's disease, Parkinson's disease, Lewy body dementia, frontotemporal dementia, and the like. In particular, Alzheimer's disease and Lewy body dementia account for 90% of all dementia patients, but despite the ongoing research and development, drugs that only help improve symptoms such as behavior, cognition, and memory improvement are used for treatment. Accordingly, until recently, the development of the therapeutic agent has been actively progressing around the world, and natural medicines, synthetic medicines, stem cell therapy, peptide medicines and the like are currently being studied in Korea, but there are no visible results yet.

SUMMARY

Embodiments of the present disclosure are directed to a use of a fermented steam-dried ginseng berry to treat neurodegenerative diseases.

Embodiments of the present disclosure are also directed to a use of a fermented steam-dried ginseng berry to improve cognitive function or protect brain.

According to an embodiment of the present disclosure, the present disclosure provides a pharmaceutical composition for preventing or treating neurodegenerative diseases includes a fermented steam-dried ginseng berry as an active ingredient.

According to another embodiment of the present disclosure, the present disclosure provides a health functional food for preventing or treating neurodegenerative diseases includes a fermented steam-dried ginseng berry as an active ingredient.

According to another embodiment of the present disclosure, the present disclosure provides a health functional food for improving cognitive function includes a fermented steam-dried ginseng berry as an active ingredient.

According to another embodiment of the present disclosure, the present disclosure provides a health functional food for protecting brain includes a fermented steam-dried ginseng berry as an active ingredient.

Advantageous Effects

The fermented steam-dried ginseng berry according to one or more embodiments of the present disclosure may have a high total ginsenoside and polyphenol content, exhibit antioxidant activity, inhibit acetylcholinesterase, improve cognitive function and spatial perception in animal model of dementias, recover acetylcholine expression and inhibit accumulation of amyloid-beta in brain tissue of the animal model of dementias, inhibit brain damage in animal model of dementias, and promote expression of genes related to brain damage in neuronal cell lines, and accordingly, the fermented steam-dried ginseng berry may be used to treat neurodegenerative diseases, improve cognitive function, and protect brain.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
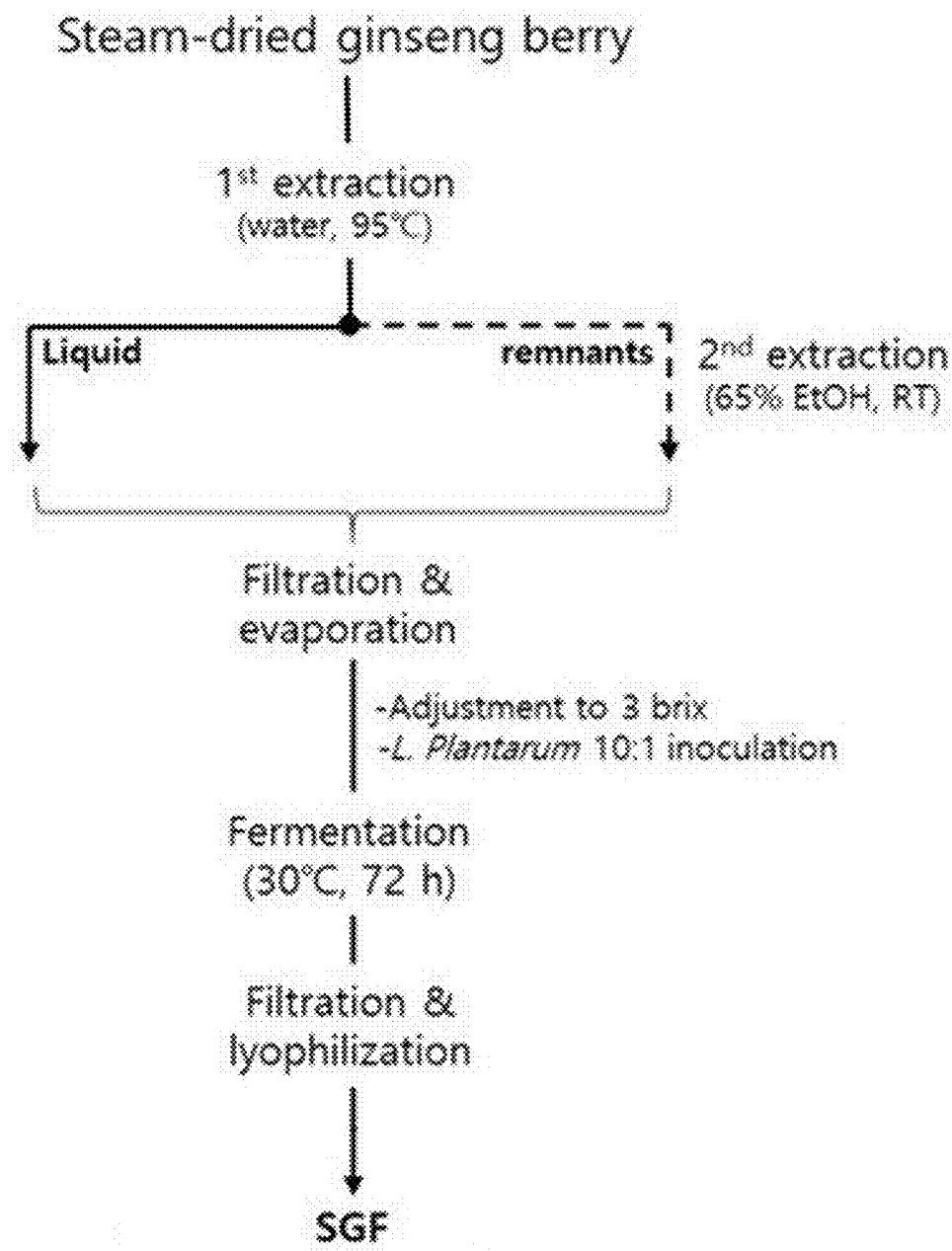
FIG. 1 is a schematic diagram illustrating a process of preparing a fermented steam-dried ginseng berry according to an embodiment of the present disclosure.

Hereinafter, embodiments of the present disclosure will be described in detail.

The present disclosure provides a pharmaceutical composition for preventing or treating neurodegenerative diseases that includes a fermented steam-dried ginseng berry as an active ingredient.

As used herein, the term "steam-drying (jeung-po)" refers to a process of steaming and drying the medicine, and when the process is repeated nine times, it is known as "9-steaming-9-drying". Steam-drying is generally a processing process to enhance or weaken activity of some herbal medicines, soften stiffness, or remove toxicity. Putting a medicinal material in a pot filled with water and heating it with low heat is called "jeung," and drying it in sunlight is called "po."

The steam-drying may be performed an appropriate number of times by a method well known in the art, and the number and method may be modified by a person skilled in the art. The steam-dried ginseng berry subject to steam-drying specific number of times may be used alone, or respective ginseng berries subject to steam-drying different number of times may be used as a mixture.

The fermented steam-dried ginseng berry may be obtained by fermenting a steam-dried ginseng berry extract. The steam-dried ginseng berry extract may be prepared by the following conventional method:

1) preparing an extract by adding an extraction solvent to a steam-dried ginseng berry;
2) filtering the extract of step 1);
3) drying the filtered filtrate of step 2) after concentration under reduced pressure.

In addition, the extraction solvent may be water, alcohol, or a mixture thereof. The alcohol may be a $C_1$ to $C_2$ lower alcohol, and specifically, the alcohol may be ethanol, methanol or spirits. The extraction solvent may be added in an amount of 5 to 30 times, 5 to 25 times, 5 to 20 times, 10 to 25 times, or 10 to 20 times of a mass of the steam-dried ginseng berry.

The extraction method may be shaking extractions, Soxhlet extractions, or reflux extraction. In such a case, the extraction time may be 1 to 70 hours, 30 to 60 hours, or 40 to 50 hours. The extraction may be repeated one or more times.

In an embodiment, the decompression concentration in step 3) may be performed using a vacuum decompression concentrator or a vacuum rotary evaporator. In addition, the drying may be decompression drying, vacuum drying, boiling drying, spray drying, or freeze drying, and specifically, freeze drying.

A pharmaceutical composition according to an embodiment of the present disclosure may be prepared by using a steam-dried ginseng berry extract extracted with a single solvent or using a mixture of extracts extracted with different types of solvents. In such a case, an extract that is extracted by adding an extraction solvent to a residue remaining after the steam-dried ginseng berry extract is extracted may be also included.

The steam-dried ginseng berry extract may be fermented by a method well known in the art, and the fermentation may be appropriately modified and performed by a person skilled in the art. Specifically, the fermentation may be performed with any one or more species selected from the group consisting of the genus *Lactobacillus* and the genus *Bacillus*. For example, the genus *Lactobacillus* may include *Lactobacillus plantarum*, *Lactobacillus brevis*, *Lactobacillus casei*, and *Lactobacillus fermentum*. In an embodiment, the genus *Bacillus* may include *Bacillus subtilius*. According to an embodiment of the present disclosure, the fermentation may be performed by a *Lactobacillus plantarum* which was deposited with the accession number KCTC21084, on Sep. 5, 2016, and also deposited under the Budapest Treaty on the International Recognition of the Deposit of Microorganisms for the Purpose of Patent Procedure at the Korean Collection for Type Cultures at Korea Research Institute of Bioscience and Biotechnology (KRIBB) of 181, Ipsin-gil, Jeongeup-si, Jeollabuk-do 56212, Republic of Korea on Nov. 30, 2020 under the accession number KCTC 14392BP.

For the preparation of the fermented steam-dried ginseng berry according to an embodiment, the strain may be inoculated in a conventional amount and fermented under conditions of an appropriate time and temperature.

The neurodegenerative disease may include all neurodegenerative diseases known in the art. Specifically, the neurodegenerative disease may be a neurodegenerative disease caused by inhibition of acetylcholine expression and accumulation of amyloid-beta. For example, the neurodegenerative diseases may include Alzheimer's disease, Parkinson's disease, Huntington disease, mild cognitive impairment, cerebral amyloid angiopathy, Down syndrome, amyloid stroke, systemic amyloid disease, senile dementia, amyotrophic lateral sclerosis, spinocerebellar atrophy, Tourette's syndrome, Friedrich's ataxia, Lewy Body dementia, progressive supranuclear palsy, or frontotemporal dementia.

The pharmaceutical composition according to an embodiment may include 10 to 95 percent by weight (wt %) of a fermented steam-dried ginseng berry, which is an active ingredient, with respect to the total weight of the composition. In addition, the pharmaceutical composition according to an embodiment may further include one or more active ingredients exhibiting the same or similar functions in addition to the active ingredients.

The pharmaceutical composition according to an embodiment may include a carrier, a diluent, an excipient, or a mixture thereof commonly used in biological preparations. Any pharmaceutically acceptable carrier may be used as long as it is suitable for delivering the composition in vivo. Specifically, the carrier may be compound, saline, sterile water, Ringer's solution, dextrose solution, maltodextrin solution, glycerol, ethanol, or a mixture thereof described in "Merck Index, 13th ed., Merck & Co. Inc.". In addition, conventional additives such as antioxidants, buffers, and bacteriostatic agents may be added as needed.

When formulating the composition, diluents or excipients such as commonly used fillers, extenders, binders, wetting agents, disintegrants, and surfactants may be added.

The composition according to an embodiment of the present disclosure may be formulated as an oral formulation or a non-oral formulation. The oral formulation may include solid formulations and liquid formulations. The solid formulation may be a tablet, pill, powder, granule, capsule or troche, and such a solid formulation may be prepared by adding at least one excipient to the composition. The excipient may be starch, calcium carbonate, sucrose, lactose, gelatin, or a mixture thereof. In addition, the solid formulation may include a lubricant, examples of which may include magnesium stearate, talc and the like. In an embodiment, the liquid formulation may be suspension, oral liquid, emulsion or syrup. In such a case, the liquid formulation may include excipients such as wetting agents, sweetening agents, fragrances, preservatives and the like.

The non-oral formulation may include injections, suppositories, powders for respiratory inhalation, aerosols for sprays, powders and creams. The injections may include a sterilized aqueous solution, a non-aqueous solvent, a suspension solvent, an emulsion, and the like. In such a case, as the non-aqueous solvent or suspension solvent, propylene glycol, polyethylene glycol vegetable oils such as olive oil, or injectable esters such as ethyl oleate may be used.

The composition according to an embodiment may be administered orally or non-orally according to the purpose of use. Non-oral administration may include intraperitoneal, rectal, subcutaneous, intravenous, intramuscular or intrathoracic injection.

The composition may be administered in a pharmaceutically effective amount. This may vary depending on the type of disease, severity, activity of the drug, the patient's sensitivity to the drug, administration time, administration route, treatment period, and other drugs used together. However, for a desirable effect, an amount of the active ingredient included in the pharmaceutical composition according to an embodiment of the present disclosure may be in a range from 0.0001 to 1,000 mg/kg, specifically 0.001 to 500 mg/kg. The administration may be one time or several times a day.

The composition according to an embodiment may be administered alone or in combination with other therapeutic agents. When administered in combination, administration may be sequential or simultaneous.

In addition, the present disclosure also provides a health functional food for preventing or improving neurodegenerative diseases that includes a fermented steam-dried ginseng berry as an active ingredient.

The fermented steam-dried ginseng berry may have the same characteristics as described above. For example, the fermented steam-dried ginseng berry may be obtained by fermenting a steam-dried ginseng berry extract, and the steam-dried ginseng berry extract may be prepared as described above. In addition, the steam-dried ginseng berry extract may be fermented in the same manner as described above, and the fermentation may be appropriately modified and performed by a person skilled in the art.

The neurodegenerative disease may have the characteristics as described above, and specifically, the neurodegenerative disease may be a neurodegenerative disease caused by inhibition of acetylcholine expression and accumulation of amyloid-beta.

The fermented steam-dried ginseng berry according to an embodiment may be added to food as it is or may be used together with other foods or food ingredients. In such a case, an amount of the active ingredient added may be determined according to the purpose of use, and generally may be in a range from 0.01 to 90 parts by weight of the total weight of the food.

The form and type of the health functional food are not particularly limited. Specifically, the health functional food may be in the form of tablets, capsules, powders, granules, liquids, and pills. The health functional food may include various flavoring agents, sweetening agents, or natural carbohydrates as additional ingredients. The sweetener may be a natural or synthetic sweetener, and examples of the natural sweetener may include taumatin and stevia extract. In an embodiment, examples of the synthetic sweeteners may include saccharin and aspartame. In addition, the natural carbohydrates may be monosaccharides, disaccharides, polysaccharides, oligosaccharides and sugar alcohols.

In addition to the above-described additional ingredients, the health functional food according to an embodiment may further includes nutrients, vitamins, electrolytes, flavoring agents, coloring agents, pectic acid and salts thereof, alginic acid and salts thereof, organic acids, protective colloidal thickeners, pH adjusters, stabilizers, preservatives, glycerin, alcohol, and the like. These components may be used alone or in combination. An amount of the additive may be selected in a range of 0.01 to 0.1 parts by weight with respect to 100 parts by weight of the composition according to an embodiment.

In addition, the present disclosure also provides a health functional food for improving cognitive function that includes a fermented steam-dried ginseng berry as an active ingredient.

The fermented steam-dried ginseng berry may have the same characteristics as described above. For example, the fermented steam-dried ginseng berry may be obtained by fermenting a steam-dried ginseng berry extract, and the steam-dried ginseng berry extract may be prepared as described above. In addition, the steam-dried ginseng berry extract may be fermented in the same manner as described above, and the fermentation may be appropriately modified and performed by a person skilled in the art.

The health functional food may have the characteristics as described above.

In addition, the present disclosure also provides a health functional food for protecting brain that includes a fermented steam-dried ginseng berry as an active ingredient.

The fermented steam-dried ginseng berry may have the same characteristics as described above. For example, the fermented steam-dried ginseng berry may be obtained by fermenting a steam-dried ginseng berry extract, and the steam-dried ginseng berry extract may be prepared as described above. In addition, the steam-dried ginseng berry extract may be fermented in the same manner as described above, and the fermentation may be appropriately modified and performed by a person skilled in the art.

The health functional food may have the characteristics as described above.

Hereinafter, the present disclosure will be described in detail with the following embodiments. However, the following embodiments are for illustrative purposes only, and the present disclosure is not limited thereto. Anything that has substantially the same configuration and achieves the same action and effects as the technical idea described in the claims herein is construed to be within the scope of the invention concept of the present disclosure.

Embodiment 1. Preparation of Steam-Dried Ginseng Berry Extract Using 4 Year Old Ginseng By using collected ginseng berries, a ginseng berry extract was prepared in the following manner.

First, ginseng berries just before ripening were collected from 4 year old ginsengs in late May 2018 (Gyeonggi-do, Korea), washed with clean water, and then dried at 50° C. using a hot air dryer (JW-500ED, Jinwoo Electronic Co., Korea) for 15 hours. A steam-drying process of steaming the ginseng berries at 95° C. for 5 hours, and then drying them at 50° C. for 1 hour was performed 4 or 7 times, thereby obtaining 4-steamed-4-dried or 7-steamed-7-dried ginseng berries. The obtained 4-steamed-4-dried or 7-steamed-7-dried ginseng berries were mixed in a weight ratio of 1:1, a distilled water in an amount of 30 times the amount was added thereto to perform hot-water extraction at 95° C. for 24 hours, and thus a hot-water extract of ginseng berries was obtained.

In addition, after obtaining the hot-water extract, a process of adding, to a remaining residue, 65% of spirits (Gyeonggi-do, Republic of Korea) in an amount of 10 times the residue and then performing extraction at room temperature for 24 hours was performed twice, and thus a spirit extract of the steam-dried ginseng berries was obtained.

Embodiment 2. Preparation of Ginseng Berry Extract Using 3 Year Old Ginseng

Except that 3 year old ginseng was used instead of 4 year old ginseng, a hot-water extract and a spirit extract of the steam-dried ginseng berry were prepared from 3 year old ginseng.

Embodiment 3. Preparation of Fermented Steam-Dried Ginseng Berry Extract Using 4 Year Old Ginseng A fermented product was prepared by inoculating *Lactobacillus plantarum* (KCTC21084) in the steam-dried ginseng berry extract using the 4 year old ginseng prepared above.

Specifically, both the hot-water extract and the spirit extract of the ginseng berries prepared in Embodiment 1 were mixed, and distilled water was added thereto, followed by diluting to be 3 brix. The diluted mixture was inoculated with *Lactobacillus plantarum* in an amount of $1 \times 10^7$ CFU/ml. The inoculated product was fermented at 30° C. for 72 hours, the fermented product was centrifuged and concentrated to 17.5 brix, and a fermented steam-dried ginseng berry extract was prepared by using ginseng berries obtained from 4 year old ginseng.

Thereafter, solid phase extraction was performed to remove polar residues included in the fermented product. Solid phase extraction was performed using YMC-TRI-ART™ C18 (YMC, Japan) according to the ginseng and ginseng products-ginsenoside content measurement-high-speed liquid chromatography method described in the standard No. KS H 2153 of the National Institute of Technology and Standards. In such a case, pre-washing was performed using 5 ml of methanol and 20 ml of water, a sample was injected so that it became 100 mg/5 ml, and then post-washing was performed with 20 ml of water and 15 ml of 30% ethanol and then eluting with 10 ml of methanol, thereby obtaining a solid extract of fermented steam-dried ginseng berries in 32.3% yield (FIG. 1).

Embodiment 4. Preparation of Fermented Steam-Dried Ginseng Berry Extract Using 3 Year Old Ginseng Except that the steam-dried ginseng berry extract that was prepared using 3 year old ginseng as in Embodiment 2 was used, a solid-phase extract of the fermented steam-dried ginseng berry was obtained in 33.1% yield (FIG. 1) using the ginseng berries obtained from 3 year old ginsengs under the same condition and method as in Embodiment 3.

Experimental Example 1. Identification of Ginsenoside Content in Fermented Steam-Dried Ginseng Berry-(1)

1-1. Identification of Total Ginsenoside Content

A content of the total ginsenosides included in the prepared fermented steam-dried ginseng berry was identified by a vanilin-sulfuric acid analysis.

Figure 2:
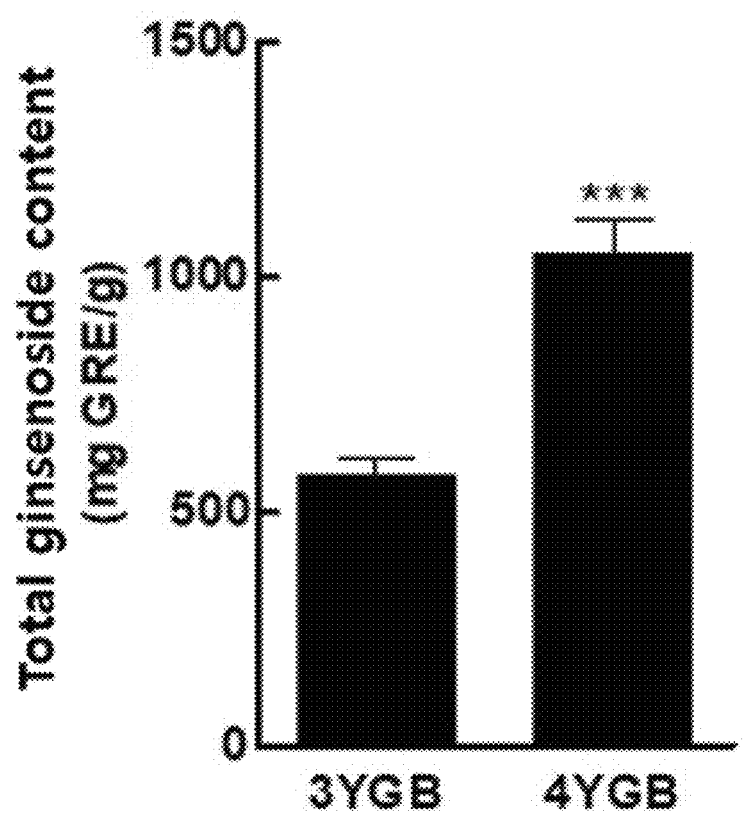
FIG. 2 is a graph illustrating results of a total ginsenoside content included in fermented steam-dried ginseng berries of 3 years old (3YGB) or 4 years old (4YGB) according to an embodiment of the present disclosure.

First, 8% of vanillin and 72% of sulfuric acid solution were mixed at a volume ratio of 6:84, placed on ice, and stored cold until use. In an embodiment, the fermented products of the steam-dried ginseng berry extracts obtained from the 4 year old or 3 year old ginseng as obtained in Embodiments 3 and 4 were prepared to a concentration of 10 mg/ml, and 10 µl of the prepared fermented product was added to a 0.2 ml tube. 90 µl of the vanillin-sulfuric acid solution was added thereto and reacted at 55° C. for 20 minutes. After the reaction was completed, the reactant was left on ice to cool, transferred to a 96-well plate, and absorbance was measured at a wavelength of 545 nm. In such a case, a calibration curve for quantifying the total ginsenoside content was plotted by diluting the standard ginsenoside Re by ½ from the concentration of 500 µg/ml to the concentration of 62.5 µg/ml. FIG. 2 shows the result of calculating the content of ginsenosides included in the fermented steam-dried ginseng berry according to an embodiment using the identified calibration curve.

As illustrated in FIG. 2, all of the fermented steam-dried ginseng berries obtained from 4 year old or 3 year old ginseng berries included a high content of ginsenoside. In particular, the total ginsenoside content in the fermented steam-dried ginseng berry obtained from 4 year old ginseng berry was about 1.7 times higher than that of 3 year old ginseng berry.

1-2. Identification of the Content of Major Ginsenosides

The contents of the major ginsenosides F4, Rg3(S), Rg3(R) and Rg5 included in the prepared fermented steam-dried ginseng berry were identified by the same conditions and methods as in Experimental Examples 1-1, and the results are shown in Table 1 below.

TABLE 1

| Sample | F4 | Rg3(S) | Rg3(R) | Rg5 | Total |
| --- | --- | --- | --- | --- | --- |
| 3 years | 30.36 | 10.60 | 5.54 | 5.94 | 52.44 |
| 4 years | 34.69 | 13.85 | 6.47 | 8.69 | 63.70 |

As illustrated in Table 1, the content of ginsenoside was significantly higher in the fermented steam-dried ginseng berry obtained from 4 year old ginseng berry compared to the fermented steam-dried ginseng berry obtained from 3 year old ginseng berry.

Experimental Example 2. Identification of Ginsenoside Content in Fermented Steam-Dried Ginseng Berry-(2)

A content of ginsenosides included in the prepared 4 year old fermented steam-dried ginseng berry was identified by high-performance liquid chromatography (HPLC) analysis. Experiments were performed using an ultimate 3000 HPLC system (Thermo Scientific, USA) and a YMC-TRIART™ C18 column (YMC, Japan). The 4 year old fermented steam-dried ginseng berry in Embodiment 3 dissolved in a concentration of 10 mg/ml as a sample was filtered using a 0.22 µm polytetrafluoroethylene (PTFE) injection filter (Hyundai Micro, Korea), and then 10 µl thereof was injected and analyzed. In such a case, the analysis conditions are illustrated in Tables 2 and 3 below.

TABLE 2

| | |
| --- | --- |
| Mobile phase | Triple distilled water (A), Acetonitrile (B) |
| Flow rate | 1.6 ml/min |
| Detector | DAD3000, 203 nm |
| Column | YMC-TRIART ™ C18 column |
| | (250 × 4.6 mm, S-5 µm, 12 nm) |
| Column temperature | 30° C. |
| Injection volume | 10 µl |

TABLE 3

| Time (min.) | Water (%) | Acetonitrile (%) |
| --- | --- | --- |
| 0-10 | 80 | 20 |
| 10-40 | 80 → 68 | 20 → 32 |
| 40-55 | 68 → 50 | 32 → 50 |
| 55-70 | 50 → 35 | 50 → 65 |
| 70-72 | 35 → 10 | 65 → 90 |
| 72-82 | 10 | 90 |
| 82-84 | 10 → 80 | 90 → 20 |
| 84-90 | 80 | 20 |

In addition, as a control group, ginsenosides Rg3(S), Rg3(R), Rg5, F4, Rg1, Re, Rb1, Rc, Rd and Rk1 (Biopurity, China) were diluted in a concentration range of 125 to 2,000 µg/ml, and a standard calibration curve was plotted and used.

Figure 3:
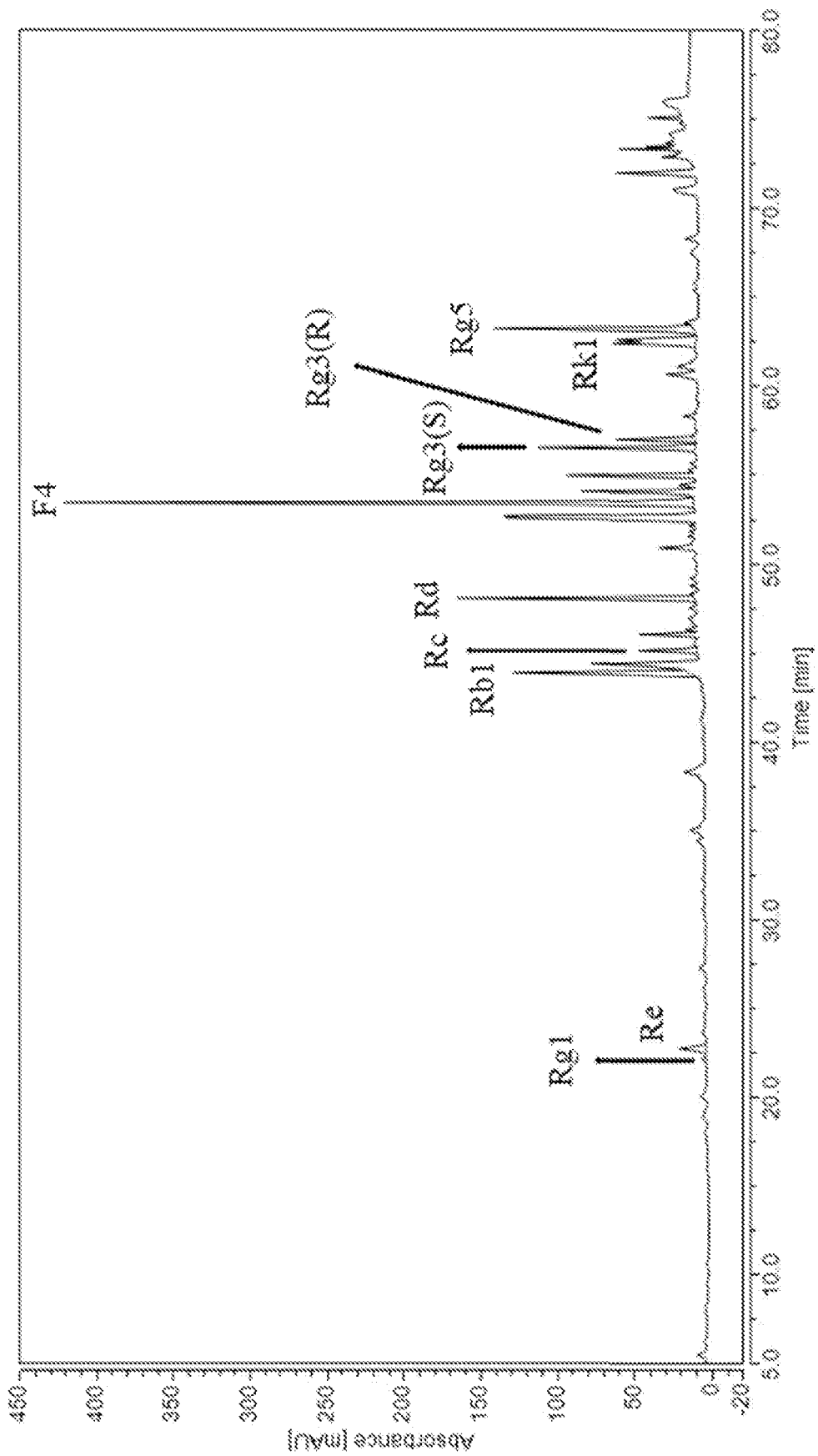
FIG. 3 is a graph illustrating HPLC analysis results of ginsenosides included in fermented steam-dried ginseng berries of 4 years old according to an embodiment of the present disclosure.

As a result, as illustrated in FIG. 3, various kinds of ginsenosides were evenly included in the fermented steam-dried ginseng berry obtained from 4 year old ginseng berry.

Experimental Example 3. Identification of Total Polyphenol Content of Fermented Steam-Dried Ginseng Berry A content of the total polyphenols included in the prepared fermented steam-dried ginseng berry was identified by applying a folin-ciocalteu analysis.

Figure 4:
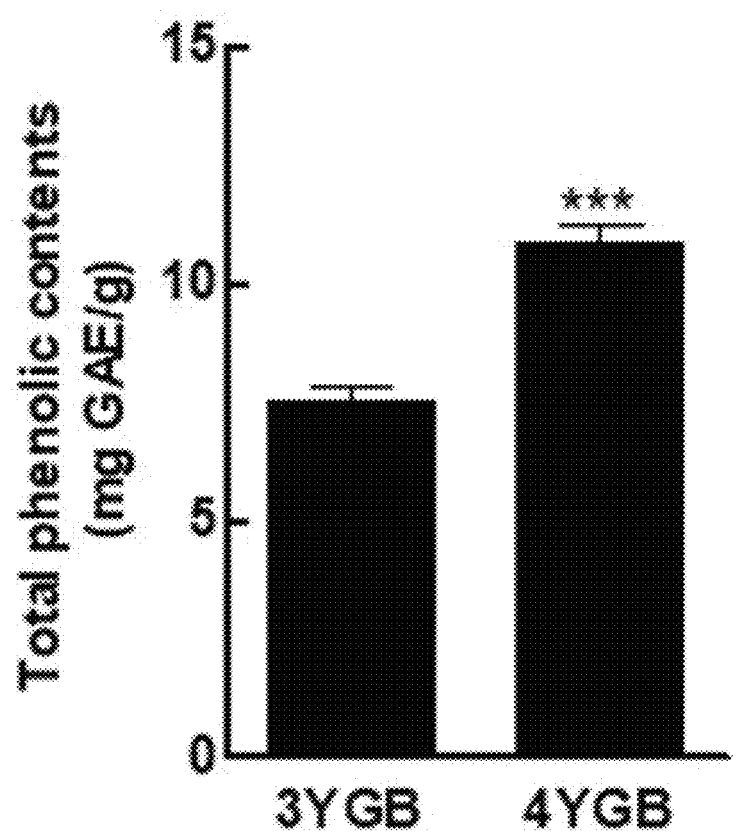
FIG. 4 is a graph illustrating results of a total polyphenol content included in fermented steam-dried ginseng berries of 3 years old (3YGB) or 4 years old (4YGB) according to an embodiment of the present disclosure.

First, a fermented product of the steam-dried ginseng berry extracts obtained from 4 year old or 3 year old ginsengs as in Embodiments 3 and 4 were prepared to a concentration of 10 mg/ml, and 10 µl thereof was added to a 0.2 ml tube. 160 µl of triple distilled water and 10 µl of folin-ciocalteu's phenol reagent (Sigma-Aldrich, USA) were mixed, and reacted in the dark for 5 minutes. After the reaction was completed, the reactant was transferred to a 96-well plate, and 20% $Na_2CO_3$ was added, followed by further reaction in the dark for 20 minutes. After the reactions, an absorbance of the 96-well plate was measured at a wavelength of 765 nm. In such a case, a calibration curve for quantifying the total polyphenol content was plotted by diluting the standard gallic acid by ½ from the concentration of 500 µg/ml to the concentration of 62.5 µg/ml. FIG. 4 shows the result of calculating the total polyphenol content in the fermented steam-dried ginseng berry according to an embodiment using the plotted calibration curve.

As illustrated in FIG. 4, a high content of polyphenol was included in the fermented steam-dried ginseng berry obtained from 3 year old or 4 year old ginseng berry, and in particular, the fermented steam-dried ginseng berry obtained from 4 year old ginseng berry include polyphenol in a higher amount than that from 3 year old ginseng berries.

Experimental Example 4. Identification of Antioxidant Activity of Fermented Steam-Dried Ginseng Berry

4-1. Identification of Radical Scavenging Ability

The antioxidant activity of the prepared fermented steam-dried ginseng berry was identified as follows through the radical scavenging ability.

First, a methanol solution including 0.3 mM of DPPH (1,1-diphenyl-2-picrylhydrazyl) was prepared, and 1, 10, 25, 50 or 100 μg/ml of the fermented steam-dried ginseng berry according to Embodiment 3 or Embodiment 4 was added thereto. After reacting the mixture at room temperature for 10 minutes, the result of calculating the radical scavenging ability by measuring absorbance under a wavelength of 517 nm is illustrated in FIGS. 5A and 5B.

Figure 5A:
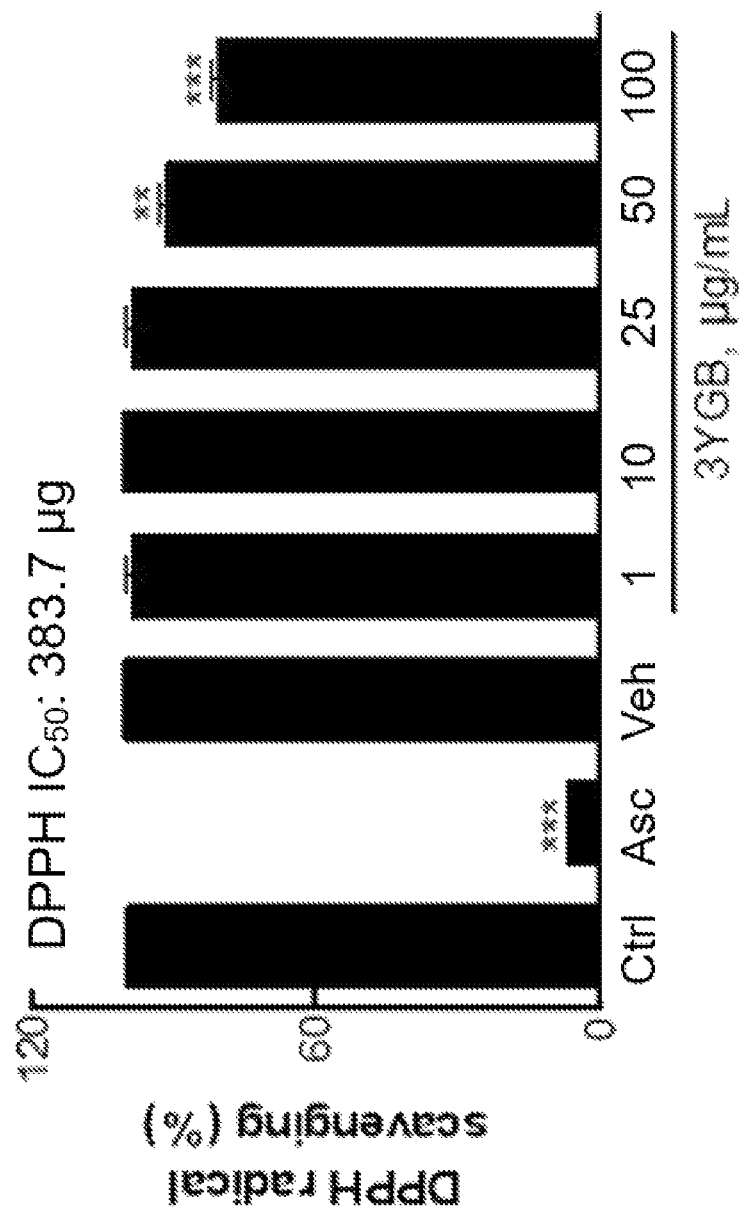
FIG. 5A and FIG. 5B are graphs illustrating results of radical scavenging effects of fermented steam-dried ginseng berries of 3 year old (FIG. 5A) or 4 year old (FIG. 5B) according to an embodiment of the present disclosure.
Figure 5B:
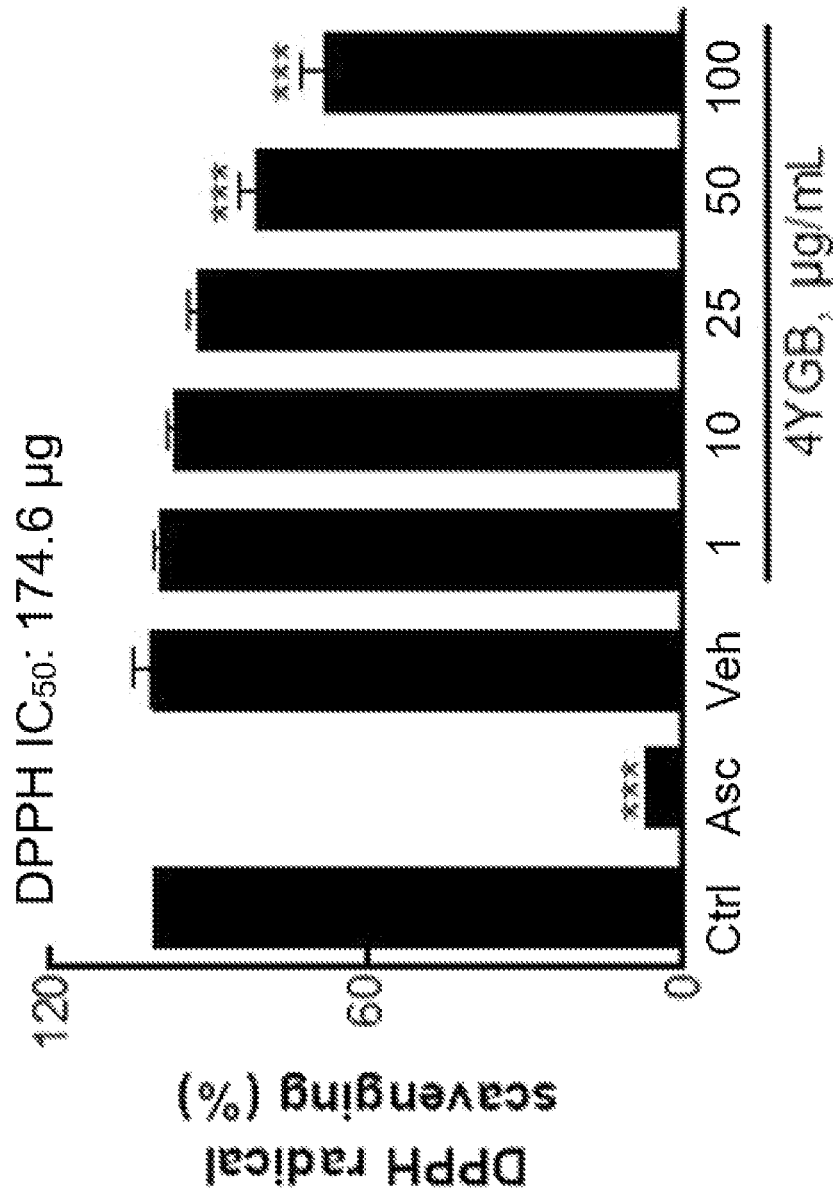

As illustrated in FIGS. 5A and 5B, the fermented steam-dried ginseng berries obtained from 3 year old or 4 year old ginseng berries exhibited DPPH IC50 of 383.7 and 174.6 μg/ml, respectively. In particular, the fermented steam-dried ginseng berry obtained from 4 year old ginseng berry showed about twice higher antioxidant activity than that from 3 year old ginseng berries.

4-2. Identification of Oxidation Inhibitory Ability of Metal Ion Catalyst

The antioxidant activity of the prepared fermented steam-dried ginseng berries was identified as follows through identification of metal ion catalyst oxidation inhibitory ability.

Specifically, a hydroxyl radical was generated by adding 100 μM of $Cu^{2+}$ and 2.5 mM of $H_2O_2$ to a solution including 0.5 μg/ml of BSA (bovine serum albumin, Sigma-Aldrich, USA). Then, 10, 50, or 100 μg/ml of the fermented steam-dried ginseng berry of Embodiment 3 or 4 was added thereto and reacted. After the reaction was completed, each of the reactants was subjected to electrophoresis on 10% sodium dedoxyl sulfate (SDS) polyacrylamide gel to identify a level of inhibition of BSA protein degradation by the fermented steam-dried ginseng berry. In such a case, 50 μM of ascorbic acid was used as a positive control.

Figure 6:
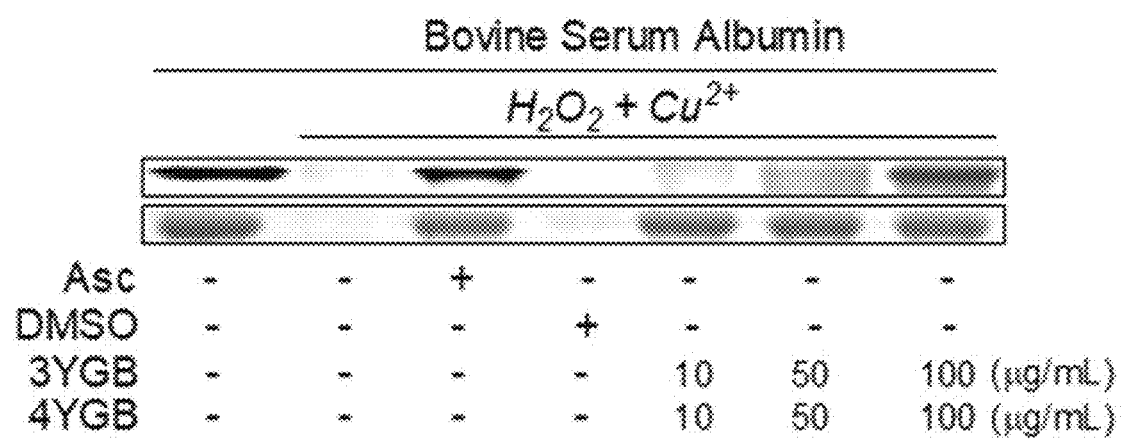
FIG. 6 is a graph illustrating results of oxidation inhibitory ability of metal ion catalyst of fermented steam-dried ginseng berries of 3 years old (3YGB) or 4 years old (4YGB) according to an embodiment of the present disclosure.

As a result, as illustrated in FIG. 6, it was appreciated that the fermented steam-dried ginseng berry obtained from the 3 year old or 4 year old ginseng berry showed excellent antioxidant activity. In particular, it was identified that the fermented steam-dried ginseng berry obtained from the 4 year old ginseng berry protected the BSA protein at a level similar to that of the positive control group even at a low concentration of 10 μg/ml, and the antioxidant activity was remarkably excellent.

Experimental Example 5. Identification of Acetylcholine Esterase Inhibitory Activity of Fermented Steam-Dried Ginseng Berry Acetylcholine esterase (AChE) inhibitory activity of the fermented steam-dried ginseng berry obtained from 4 year old ginseng berry having high total saponin content and polyphenol content and excellent antioxidant activity was identified as follows.

First, a 7-week-old male ICR mouse (Daehan Bio Link, Korea) was anesthetized through ether inhalation, and euthanized by perfusion of 10 ml of sterile physiological saline to the heart. A brain tissue was removed from the euthanized mouse by a conventional method, and then 100 mM of cold PBS was added thereto, followed by disruption with a tissue disruptor (polytron PT-MR 2100, Luzern, Switzerland) to obtain a 5% homogenate. Meanwhile, acetylthiocholine iodide (Sigma-Aldrich, USA) and DTNB (5,5'-dithiobis-(2-nitrobenzoic acid), Sigma-Aldrich, USA) were dissolved in PBS and ethanol at a concentration of 0.5 mM, respectively. In addition, the fermented steam-dried ginseng berry of Embodiment 4 was prepared at a concentration of 1, 3, 6, 12.5, 25, 50 or 100 μg/ml, and PBS was used as a negative control.

10 μl of the acetylthiocholine iodine solution, 10 μl of the DTNB solution, 30 μl of the disrupted mouse brain homogenate, and 50 μl of the prepared fermented steam-dried ginseng berry were mixed in a cuvette, and PBS was added so that the final volume was 500 μl. A change in absorbance (ΔOD/min) was measured for a total of 3 minutes at 1 minute intervals under a wavelength of 412 nm, and the result of calculating a rate of inhibiting acetylcholine esterase activity with respect to a value of the negative control as 100% was illustrated in 7.

Figure 7:
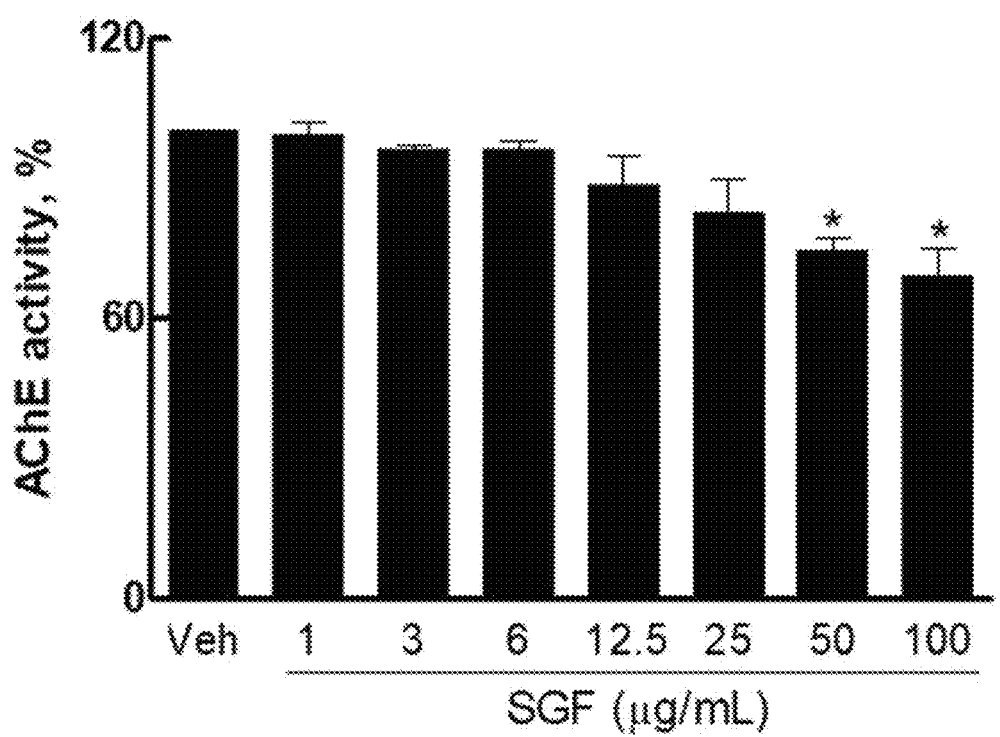
FIG. 7 is a graph illustrating results of acetylcholine esterase inhibitory activity of a fermented steam-dried ginseng berry (SGF) according to an embodiment of the present disclosure.

As illustrated in FIG. 7, the fermented steam-dried ginseng berry according to an embodiment inhibited acetylcholine esterase in a concentration-dependent manner, and in particular, the group treated with the fermented steam-dried ginseng berry at a concentration of 25, 50 or 100 μg/ml showed significant effects.

Accordingly, from the above, it was appreciated that the fermented steam-dried ginseng berry according to an embodiment exhibited an effect of improving cognitive ability by inhibiting acetylcholine esterase.

Experimental Example 6. Improvement of Cognitive Function by Fermented Steam-Dried Ginseng Berry

6-1. Preparation of Animal Model of Dementia and Administration of Fermented Steam-Dried Ginseng Berry In order to identify the improvement of the cognitive function of the fermented steam-dried ginseng berry, an animal model of dementia was firstly prepared by the following method.

First, 6-week-old ICR male mice (C57BL/6J, DBL Co. Ltd., Korea) weighing around 25 g were purchased, and the mice were randomly distributed into 6 groups, each group with 8 mice. The mice were bred in an air-conditioned semi-SPF room under the conditions of a temperature of 23±2° C., a relative humidity of 55±10%, ventilation times of 12 times/hour, lighting cycle of 12 hours, and 150 to 300 Lux illumination. This experiment was carried out according to the standard work guidelines of the Animal Test Ethics Committee (CBNUR-1287-19) of the laboratory animal research support center of Chungbuk National University under the approval of the same committee.

A test substance was administered to the mice from 1 week after breeding. The fermented steam-dried ginseng berry was orally administered at a dose of 100, 300 or 500 mg/kg daily for 6 weeks. In such a case, 100 mg/kg of EGCG (epigallocatechin gallate) treatment group was used as a positive control group, and no treatment group not treated with anything and amyloid-beta (amyloid-β, $Aβ_{1-42}$) treated group administered only with amyloid-beta were used as a negative control group (Table 5).

TABLE 5

| Group | administered drug and dose | Number of animals |
|---|---|---|
| Non-treated group | Distilled water | 9 |
| Amyloid-beta treated group | Distilled water | 9 |
| Fermented steam-dried ginseng berry 100 | 100 mg/kg | 6 |
| Fermented steam-dried ginseng berry 300 | 300 mg/kg | 8 |
| Fermented steam-dried ginseng berry 500 | 500 mg/kg | 7 |
| EGCG 100 | 100 mg/kg | 6 |

On the last day of administration of the test substance, mice were anesthetized by ether inhalation and fastened in a stereotaxic frame (Stoelting, USA). Dementia was induced by administration of 5 μl of 5 mg/ml of amyloid-beta into the ventricle of the fastened mouse (AP: 0.6, ML: 1.1, DV: 2.0 mm).

Body weight was measured every day during the administration period to determine abnormal symptoms, but no significant body weight change was observed.

6-2. Passive Avoidance Test (PAT)

The effect of improving cognitive function of mice administered with the fermented steam-dried ginseng berry and amyloid-beta which is a dementia-inducing substance in Experimental Example 6-1, was identified through a passive avoidance test. The passive avoidance test was measured 6 times at 2 hour intervals from 48 hours after amyloid-beta administration.

First, a mouse was placed in a bright room of a passive spinning box divided into a dark room and a bright room, and when the mouse moved to the dark room, an electric shock was applied for 2 seconds at an intensity of 1 mA. While repeating this, memory capacity of the mouse was evaluated by measuring the time the mouse stayed in the bright room. In particularly, when the mouse stayed in the bright room for more than 180 seconds, it was identified that the memory of the mouse was formed.

Figure 8:
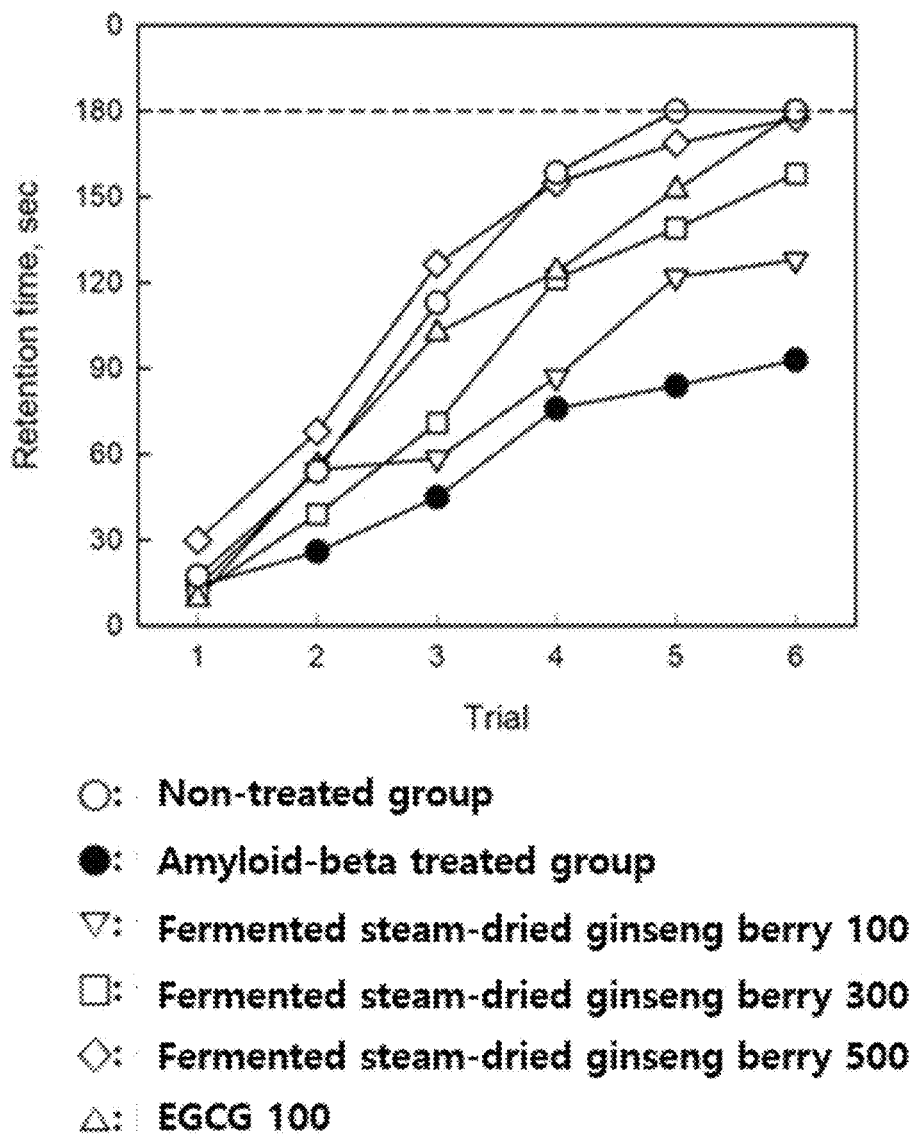
FIG. 8 is a graph illustrating results of cognitive function improvement activity of a fermented steam-dried ginseng berry (SGF) for an animal model of dementia according to an embodiment of the present disclosure.

As a result, as illustrated in FIG. 8, as the number increases, the time during which the mice in the untreated group without any treatment stays in the bright room gradually increased, and in the fifth round, the memory was completely formed by staying for 180 seconds or more. On the other hand, the amyloid-beta-treated group treated with amyloid-beta only showed poor memory formation by learning until the 6th round.

In the group treated with the fermented steam-dried ginseng berry according to an embodiment, the decrease in cognitive function reduced by amyloid-beta was dose-dependently increased. In particular, the administration group administered with the fermented steam-dried ginseng berry at a dose of 500 mg/kg recovered memory to a normal level and showed high efficacy similar to the positive control EGCG.

6-3. Morris Water-Maze Test (MWMT)

The effect of improving spatial perception ability of mice administered with the fermented steam-dried ginseng berry and the dementia-inducing substance amyloid-beta in Experimental Example 1, was identified through a Morris water-maze test. The Morris water-maze test was conducted once a day for 6 days in which the fermented steam-dried ginseng berries were administered.

First, a circular water tank was filled with water at a temperature of 22±2° C., and styrofoam was put therein to cover a platform for refuge under the water surface. The mouse was put in water, and the time it took for the mouse to memorize markers around the tank and visit the platform located at a certain place in the tank was measured. In such a case, when the mouse could not find the platform even after 180 seconds, they was allowed to stay on the platform for 30 seconds to induce memory.

Figure 9:
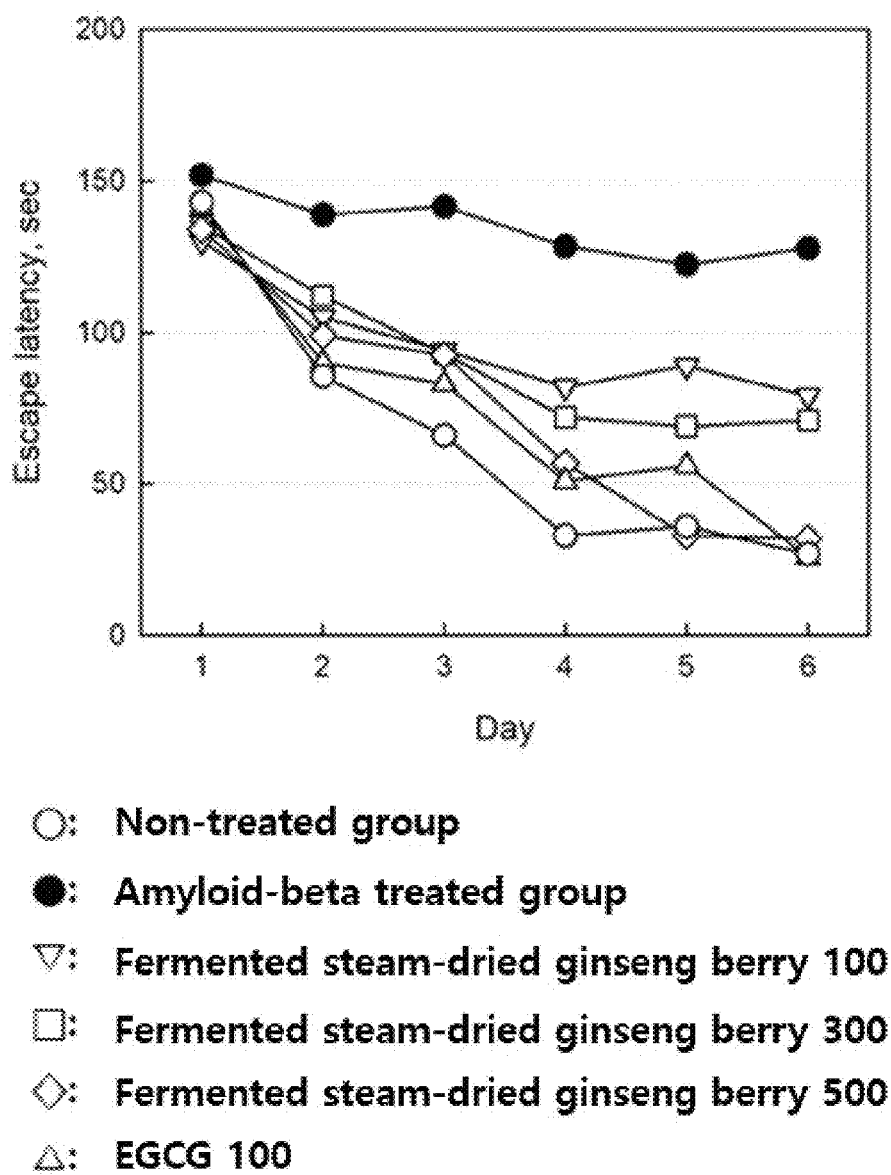
FIG. 9 is a graph illustrating results of effects of a fermented steam-dried ginseng berry (SGF) improving spatial perception ability in an animal model of dementia according to an embodiment of the present disclosure.

As a result, as illustrated in FIG. 9, as the test time increases, the time for the mice in the untreated group to visit the platform was shortened and reached within 30 seconds on the fourth day. On the other hand, the amyloid-beta-treated group treated with amyloid-beta only did not recover spatial perception until the 6th round.

In the group treated with the fermented steam-dried ginseng berry according to an embodiment, the spatial perception ability reduced by amyloid-beta was recovered in a dose-dependent manner. In particular, the administration group administered with the fermented steam-dried ginseng berry at a dose of 500 mg/kg recovered spatial perception to a normal level and showed high efficacy similar to the positive control EGCG.

Accordingly, from the above, it was identified that the fermented steam-dried ginseng berry according to an embodiment may improve cognitive function or spatial perception and may be used in the treatment of dementia.

Experimental Example 7. Identification of Effect of Fermented Steam-Dried Ginseng Berry for Recovering Acetylcholine in Brain Tissue It was identified by the following method whether the fermented steam-dried ginseng berry increases concentration of acetylcholine in brain tissue.

Specifically, a brain of the mouse to which the fermented steam-dried ginseng berry was administered in Experimental Example 6 was removed by sufficient perfusion of the brain using cold saline after all experiments were completed. The extracted brain tissue was frozen and stored in liquid nitrogen, the weight was measured on the day of the experiment, and then, 10 times the volume of cold PBS was added and homogenized using a homogenizer. The homogenized homogenate was analyzed using an AMPLEX™ Red acethylcholine/acetylcholine esterase assay kit (Invitrogen, USA) according to the manufacturer's protocol, and the results are shown in FIG. 10.

Figure 10:
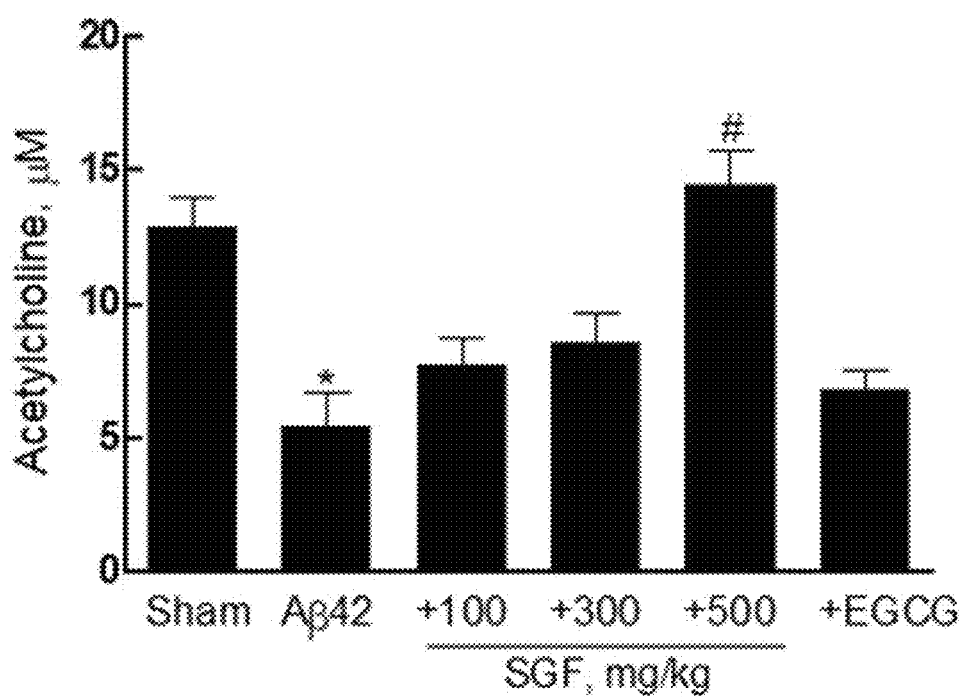
FIG. 10 is a graph illustrating results of acetylcholine recovery activity of a fermented steam-dried ginseng berry (SGF) in brain tissue in an animal model of dementia according to an embodiment of the present disclosure.

As illustrated in FIG. 10, the concentration of acetylcholine in the brain was significantly decreased in the amyloid-beta-treated group compared to the untreated group. However, the decreased concentration of acetylcholine increased depending on the treatment concentration of the fermented steam-dried ginseng berry, and the concentration of acetylcholine recovered to the normal level in the group administered with the fermented steam-dried ginseng berry at a dose of 500 mg/kg.

Experimental Example 8. Identification of Regulation of Amyloid-Beta Expression in Brain Tissue by Fermented Steam-Dried Ginseng Berry It was identified by the following method whether the fermented steam-dried ginseng berry regulates expression of amyloid-beta in brain tissue. The experiment was performed by Western blot by a conventional method or by using an A131_42 ELISA kit (IBL, Japan) according to the manufacturer's protocol, using the brain tissue extracted in Experimental Example 7. As a result, the result of identifying the expression level of amyloid-beta by Western blot is illustrated in FIG. 11A, and the result by ELISA is illustrated in FIG. 11B.

Figure 11A:
FIG. 11A and FIG. 11B are graphs illustrating results of a fermented steam-dried ginseng berry (SGF) regulating amyloid-beta expression in brain tissue in an animal model of dementia according to an embodiment of the present disclosure, identified in a Western blot (FIG. 11A) or ELISA (FIG. 11B) scheme.
Figure 11B:
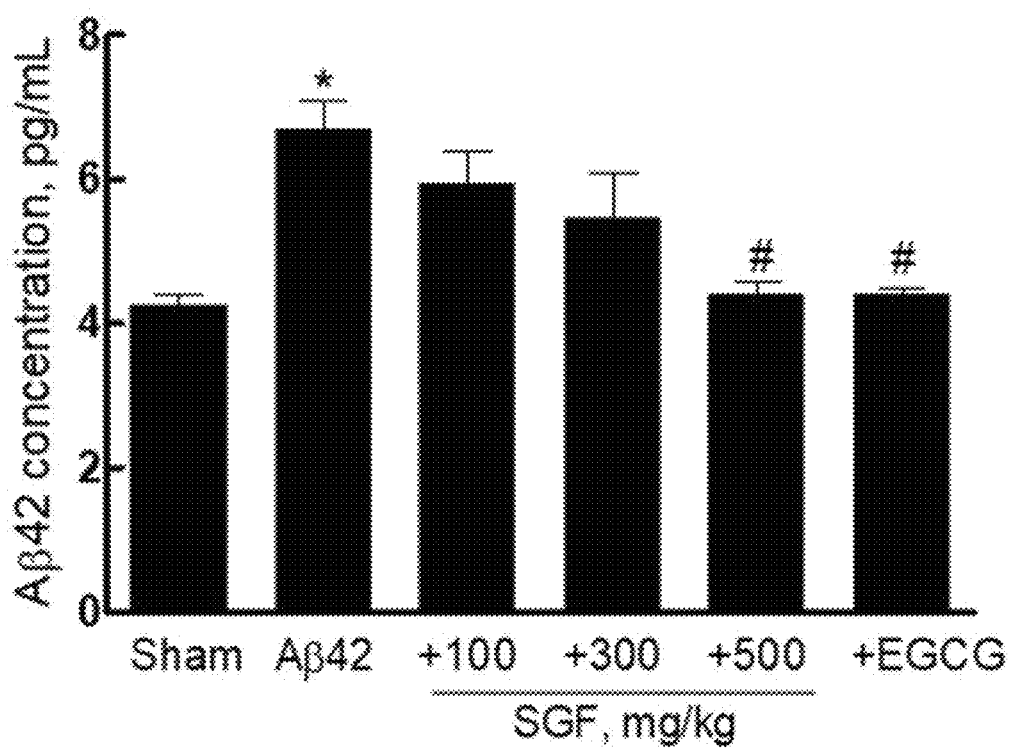

As illustrated in FIGS. 11A and 11B, an amount of amyloid-beta in the brain increased by the amyloid-beta treatment decreased depending on the treatment concentration of the fermented steam-dried ginseng berry. In particular, the amount of amyloid-beta was significantly decreased in the brain tissue of mice to which the fermented steam-dried ginseng berries were administered at a dose of 300 mg/kg or more.

From the above, it was identified that the fermented steam-dried ginseng berry according to an embodiment has brain protective activity by inhibiting accumulation of amyloid-beta in the brain tissue.

Experimental Example 9. Identification of Brain Damage Inhibitory Activity of Fermented Steam-Dried Ginseng Berry Whether the fermented steam-dried ginseng berry has an effect to inhibit brain damage was identified through a change in expression of glial fibrillary acidic protein (GFAP) protein, a biomarker in the damaged brain.

Specifically, the brain tissue extracted by the same method and conditions as described in Experimental Example 7 was fixed in a 4% paraformaldehyde solution to prepare a frozen tissue slide. The slide was immunostained with an anti-GFAP (Abcam, USA) antibody as a primary antibody and a secondary antibody (Molecular Probes, USA) bonded with Alexa Fluor-488, and cell nuclei were stained with DAPI (4'-6-diamidino-2-phenylindole). Immunostaining was performed by a conventional method, and the result of photographing the stained cells is illustrated in FIG. 12.

Figure 12:
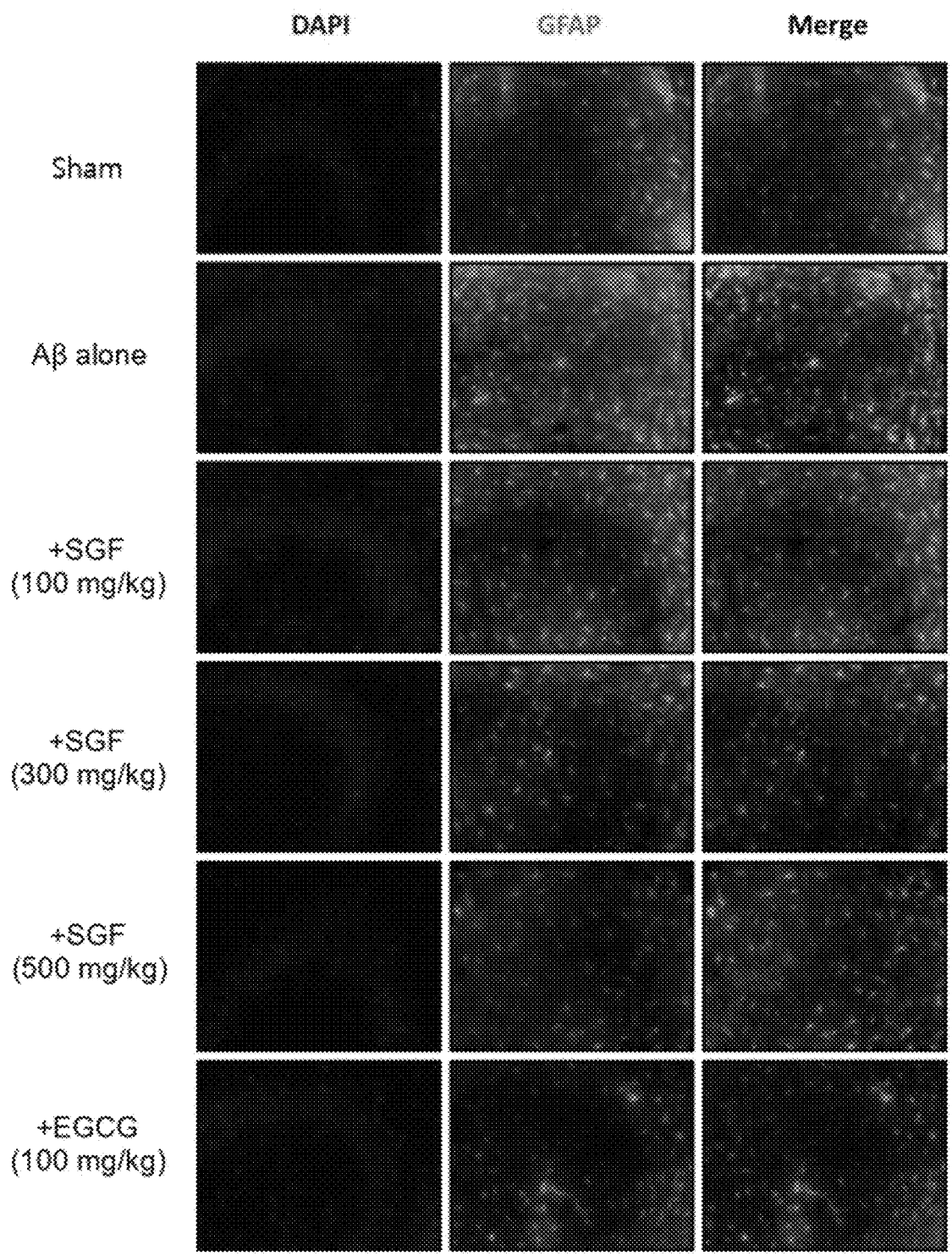
FIG. 12 is a graph illustrating results of effects of a fermented steam-dried ginseng berry (SGF) inhibiting brain damage in an animal model of dementia according to an embodiment of the present disclosure.
Figure 13A:
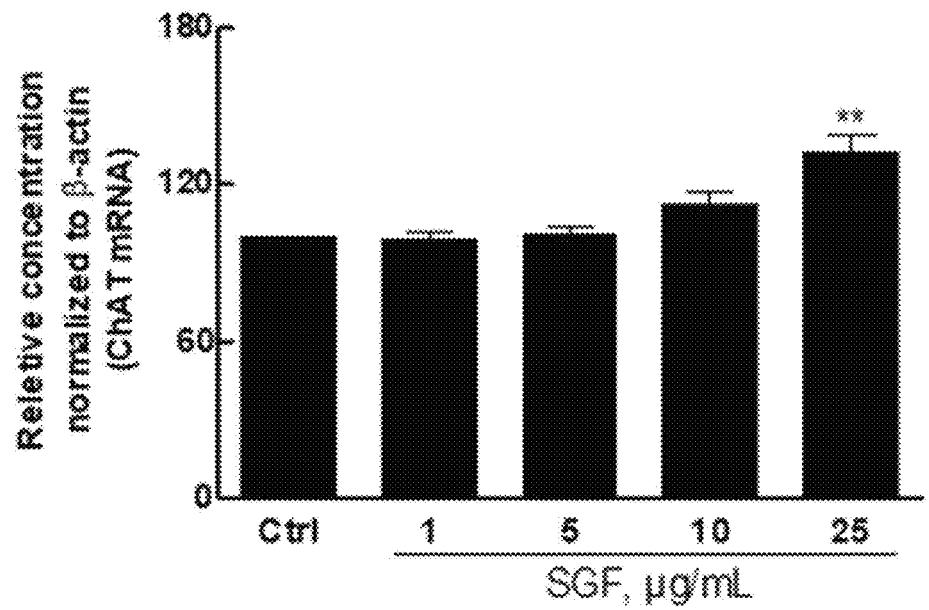
FIGS. 13A-13F are diagrams illustrating results of activity of a fermented steam-dried ginseng berry (SGF) promoting expression of brain damage-related genes ChAT (FIG. 13A), VAChT (FIG. 13B) or BDNF (FIG. 13C) in a neuronal cell line according to an embodiment of the present disclosure.
Figure 13B:
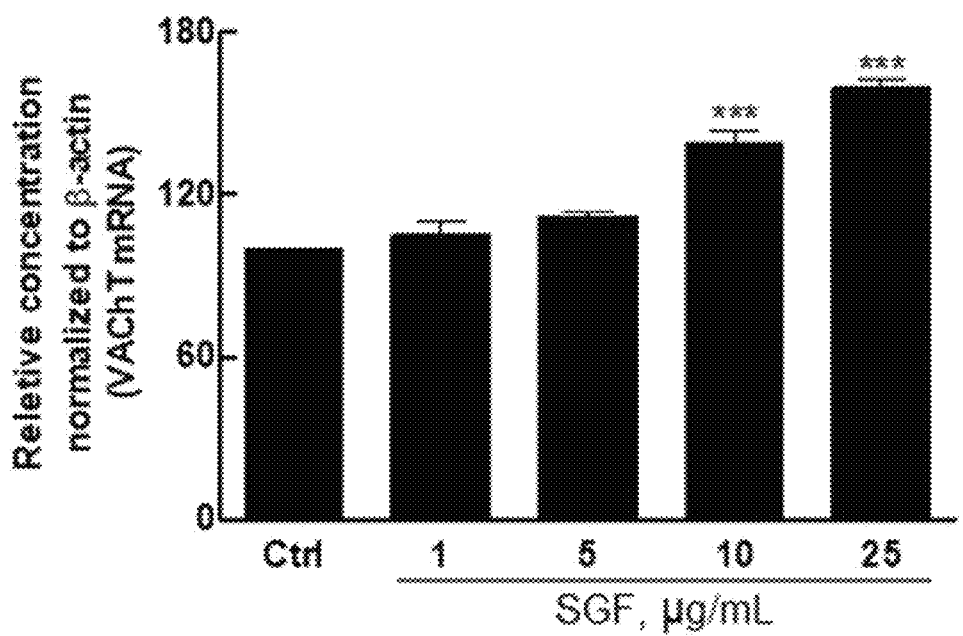
Figure 13C:
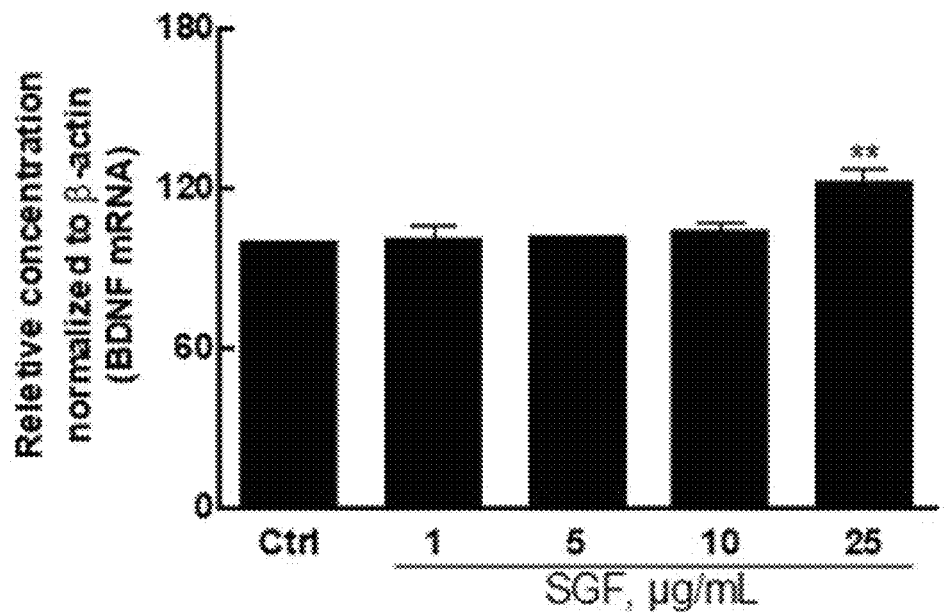
Figure 13D:
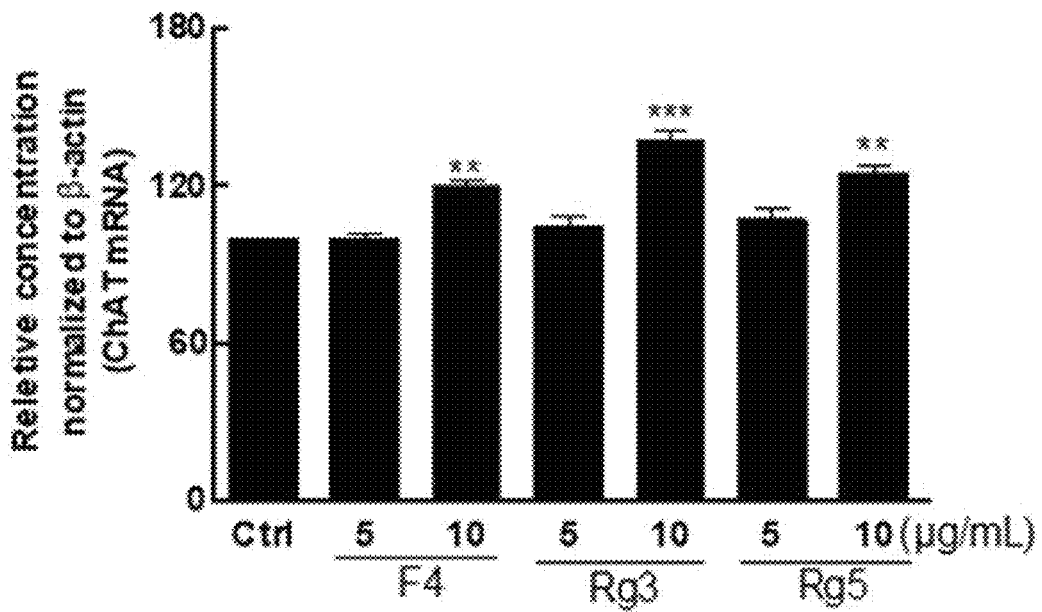
Figure 13E:
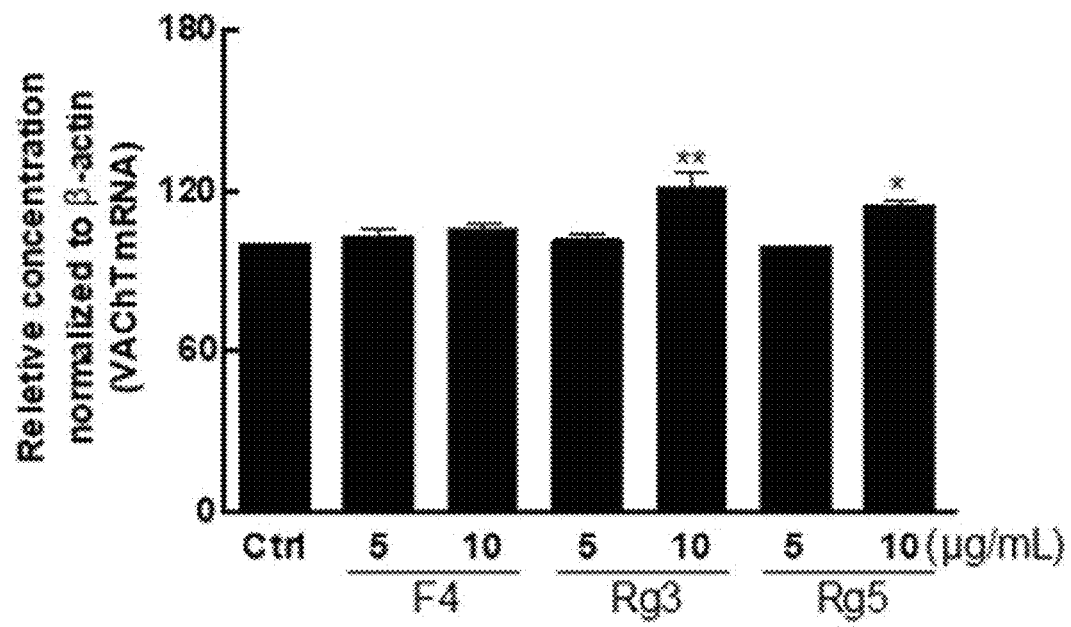
Figure 13F:
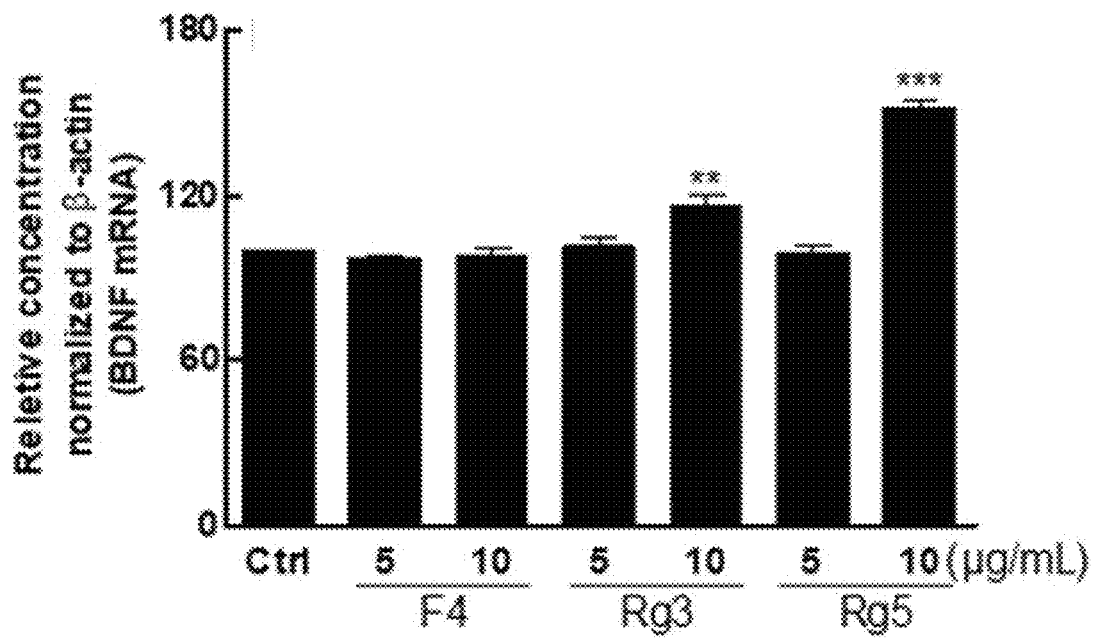

As illustrated in FIG. 12, the amyloid-beta-treated group had an average of 412 astrocytes in which the GFAP protein was expressed in the brain tissue, which was increased by 4.7 times compared to 87 in the non-treated group. However, this decreased depending on the treatment concentration of the fermented steam-dried ginseng berry. In particular, the group administered with the fermented steam-dried ginseng berry at a dose of 500 mg/kg recovered the expression of GFAP protein to a normal level.

Experimental Example 10. Identification of Regulation of Brain-Protection Gene Expression by Fermented Steam-Dried Ginseng Berry Changes in expression of genes involved in inhibition of brain damage, such as choline acetyltransferase (ChAT), vasicular acetylcholine transporter (VAChT), and brain-derived neurotrophic factor (BDNF) genes, were identified by qPCR.

First, a Neuro-2a (N2a) cell line, a neuronal cell line of a mouse, was prepared by culturing under conditions of 37° C. and 5% of $CO_2$ using DMEM (Dulbecco's Modified Eagle Medium, Hyclone, USA) medium supplemented with 10% of fetal calf serum. In such a case, it was used when the cultured cells proliferated to about 90% of the culture dish, and it was regulated so as not to exceed 20 passages. The prepared cells were seeded so as to be $1.5 \times 10^6$ cells per well in a 6-well plate and cultured overnight. The next day, the cultured cells were treated with the fermented steam-dried ginseng berry to a concentration of 1, 5, 10 or 25 μg/ml and further cultured for 24 hours. In such a case, an untreated control group was used as a control group.

The cells were lysed by adding 1 ml of a trizol (Life Technologies, USA) reagent to the cultured cells, and allowed to stand at room temperature. After 5 minutes, 200 μl of chloroform was added thereto, followed by centrifugation for 15 minutes under the conditions of 13,500 rpm to take 500 μl of a supernatant. RNA was precipitated by adding 500 μl of isopropyl alcohol to the supernatant and centrifuging for 10 minutes under the condition of 13,500 rpm. The precipitated RNA was washed with 0.75 ml of 75% ethanol diluted with DEPC (diethyl pyrocarbonate, Sigma-Aldrich, USA) distilled water, and then dried in air to obtain RNA. Reverse transcription was performed using 1 μg of the RNA as a template using an IMPROM™-II reverse transcription system (Promega, USA) and an oligo dT primer. By using primers illustrated in Table 6 and ROTOR-GENE™ 6000 (Rotor-Gene 6000, Qiagen, USA) with the obtained cDNA as a template, qPCR was performed to quantitatively identify expression of ChAT, VAChT and BDNF genes. The expression levels of the identified genes are illustrated in FIGS. 13A-13F as a relative value normalized to the expression level of the β-actin gene.

TABLE 6

| Primer | Sequence (5' → 3') | SEQ. ID |
|---|---|---|
| iNOS_forward | TGCCCCTGGAAGTTTCTCTT | SEQ. ID. NO: 1 |
| iNOS_reverse | ACTGCCCCAGTTTTTGATCC | SEQ. ID. NO: 2 |
| ChAT_forward | CCTGCCAGTCAACTCTAGCC | SEQ. ID. NO: 3 |
| ChAT_reverse | GGAAGCCGGTATGATGAGAA | SEQ. ID. NO: 4 |
| VAChT_forward | TTGATCGCATGAGCTACGAC | SEQ. ID. NO: 5 |
| VAChT_reverse | CCACTAGGCTTCCAAAGCTG | SEQ. ID. NO: 6 |
| BDNF_forward | ATGCTCAGCAGTCAAGTGCC | SEQ. ID. NO: 7 |
| BDNF_reverse | TTTTATCTGCCGCTGTGACC | SEQ. ID. NO: 8 |
| β-actin_forward | TACAGCTTCACCACCACAGC | SEQ. ID. NO: 9 |
| β-actin_reverse | AAGGAAGGCTGGAAAAGAGC | SEQ. ID. NO: 10 |

As illustrated in FIGS. 13A-13F, the expression of ChAT, VAChT, and BDNF genes increased depending on the treatment concentration of the fermented steam-dried ginseng berry.

Availability of Deposited Microorganism. *Lactobacillus plantarium* strain JLP-N2 described in this application was deposited at Korean Collection For Type Cultures (KCTC) at Korea Research Institute of Bioscience and Biotechnology (KRIBB) of 181 Ipsin-gil, Jeongeup-si, Jeonbuk 56212, Republic of Korea under Accession Number KCTC 21084 on Sep. 5, 2016 and also deposited under the Budapest Treaty on the International Recognition of the Deposit of Microorganisms for the Purpose of Patent Procedure at the KCTC under Accession Number KCTC 14392BP on Nov. 30, 2020. Upon allowance and issuance of this Application into a United States Patent, restrictions on availability of the deposit will be irrevocably removed. The deposited microorganism will be maintained for a period of 30 years, or 5 years after the last request for the deposit, or for the effective life of any patent which issues on the above-identified Application, whichever is longer. If the deposit becomes non-viable, it will be replaced and the deposit is available for access by one determined by the Commissioner to be entitled thereto under 37 C.F.R. § 1.14 and 35 U.S.C. § 122.

What is claimed is:

1. A method for treating a subject with a neurodegenerative disease comprising administering an effective amount of a composition comprising a fermented steam-dried *ginseng* berry as an active ingredient to the subject, wherein the administering inhibits and/or improves symptoms of the neurodegenerative disease.

2. The method of claim 1,
wherein the fermented steam-dried ginseng berry is obtained by fermenting a steam-dried ginseng berry extract with a *Lactobacillus planarum*.

3. The method of claim 2,
wherein the *Lactobacillus planarum* is *Lactobacillus plantarum* deposited with accession number KCTC 14392BP.

4. The method of claim 2,
wherein the ginseng berry extract is obtained employing an extraction solvent selected from the group consisting of water, $C_1$ to $C_2$ lower alcohol, and a mixture thereof.

5. The method of claim 4,
wherein the $C_1$ to $C_2$ lower alcohol is ethanol, methanol, a distilled spirit, or a mixture thereof.

6. The method of claim 1, wherein the neurodegenerative disease is Alzheimer's disease, Parkinson's disease, Huntington disease, mild cognitive impairment, cerebral amyloid angiopathy, Down syndrome, amyloid stroke, systemic amyloid disease, senile dementia, amyotrophic lateral sclerosis, spinocerebellar atrophy, Tourette's syndrome, Friedrich's ataxia, Lewy Body dementia, progressive supranuclear palsy, or frontotemporal dementia.

7. The method of claim 2, wherein the neurodegenerative disease is Alzheimer's disease, Parkinson's disease, Huntington disease, mild cognitive impairment, cerebral amyloid angiopathy, Down syndrome, amyloid stroke, systemic amyloid disease, senile dementia, amyotrophic lateral sclerosis, spinocerebellar atrophy, Tourette's syndrome, Friedrich's ataxia, Lewy Body dementia, progressive supranuclear palsy, or frontotemporal dementia.

8. The method of claim 3, wherein the neurodegenerative disease is Alzheimer's disease, Parkinson's disease, Huntington disease, mild cognitive impairment, cerebral amyloid angiopathy, Down syndrome, amyloid stroke, systemic amyloid disease, senile dementia, amyotrophic lateral sclerosis, spinocerebellar atrophy, Tourette's syndrome, Friedrich's ataxia, Lewy Body dementia, progressive supranuclear palsy, or frontotemporal dementia.

9. The method of claim 4, wherein the neurodegenerative disease is Alzheimer's disease, Parkinson's disease, Huntington disease, mild cognitive impairment, cerebral amyloid angiopathy, Down syndrome, amyloid stroke, systemic amyloid disease, senile dementia, amyotrophic lateral sclerosis, spinocerebellar atrophy, Tourette's syndrome, Friedrich's ataxia, Lewy Body dementia, progressive supranuclear palsy, or frontotemporal dementia.

10. The method of claim 5, wherein the neurodegenerative disease is Alzheimer's disease, Parkinson's disease, Huntington disease, mild cognitive impairment, cerebral amyloid angiopathy, Down syndrome, amyloid stroke, systemic amyloid disease, senile dementia, amyotrophic lateral sclerosis, spinocerebellar atrophy, Tourette's syndrome, Friedrich's ataxia, Lewy Body dementia, progressive supranuclear palsy, or frontotemporal dementia.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: iNOS_forward primer

<400> SEQUENCE: 1
tgcccctgga agtttctctt                                                                  20

<210> SEQ ID NO 2
<211> LENGTH: 20
<212> TYPE: DNA
<213> ORGANISM: Artificial Sequence
<220> FEATURE:
<223> OTHER INFORMATION: iNOS_reverse primer

<400> SEQUENCE: 2
actgccccag tttttgatcc                                                                  20

<210> SEQ ID NO 3
<211> LENGTH: 20
<212> TYPE: DNA
<213> ORGANISM: Artificial Sequence
<220> FEATURE:
<223> OTHER INFORMATION: ChAT_forward primer

<400> SEQUENCE: 3
cctgccagtc aactctagcc                                                                  20

<210> SEQ ID NO 4
<211> LENGTH: 20
<212> TYPE: DNA
<213> ORGANISM: Artificial Sequence
<220> FEATURE:
<223> OTHER INFORMATION: ChAT_reverse primer

<400> SEQUENCE: 4
ggaagccggt atgatgagaa                                                                  20

<210> SEQ ID NO 5
<211> LENGTH: 20
<212> TYPE: DNA
<213> ORGANISM: Artificial Sequence
<220> FEATURE:
<223> OTHER INFORMATION: VAChT_forward primer

<400> SEQUENCE: 5
ttgatcgcat gagctacgac                                                                  20

<210> SEQ ID NO 6
<211> LENGTH: 20
<212> TYPE: DNA
<213> ORGANISM: Artificial Sequence
<220> FEATURE:
<223> OTHER INFORMATION: VAChT_reverse primer

<400> SEQUENCE: 6
ccactaggct tccaaagctg                                                                  20

<210> SEQ ID NO 7
<211> LENGTH: 20
<212> TYPE: DNA
<213> ORGANISM: Artificial Sequence

```
<220> FEATURE:
<223> OTHER INFORMATION: BDNF_forward primer

<400> SEQUENCE: 7
atgctcagca gtcaagtgcc                                                 20

<210> SEQ ID NO 8
<211> LENGTH: 20
<212> TYPE: DNA
<213> ORGANISM: Artificial Sequence
<220> FEATURE:
<223> OTHER INFORMATION: BDNF_reverse primer

<400> SEQUENCE: 8
ttttatctgc cgctgtgacc                                                 20

<210> SEQ ID NO 9
<211> LENGTH: 20
<212> TYPE: DNA
<213> ORGANISM: Artificial Sequence
<220> FEATURE:
<223> OTHER INFORMATION: beta-actin_forward primer

<400> SEQUENCE: 9
tacagcttca ccaccacagc                                                 20

<210> SEQ ID NO 10
<211> LENGTH: 20
<212> TYPE: DNA
<213> ORGANISM: Artificial Sequence
<220> FEATURE:
<223> OTHER INFORMATION: beta-actin_reverse primer

<400> SEQUENCE: 10
aaggaaggct ggaaaagagc                                                 20
```